United States Patent [19]

Li

[11] Patent Number: 4,713,136

[45] Date of Patent: Dec. 15, 1987

[54] METHOD FOR MAKING A SPONGE COLLECTING DEVICE

[75] Inventor: Felipe S. Li, Lake Zurich, Ill.

[73] Assignee: The Kendall Company, Boston, Mass.

[21] Appl. No.: 769,652

[22] Filed: Aug. 27, 1985

Related U.S. Application Data

[60] Continuation of Ser. No. 407,391, Aug. 12, 1982, abandoned, which is a division of Ser. No. 223,187, Jan. 7, 1981, abandoned.

[51] Int. Cl.[4] ........................ B32B 31/08; B32B 31/18

[52] U.S. Cl. .................................... 156/229; 156/270; 156/308.4; 493/199; 493/931

[58] Field of Search ............... 156/229, 270, 250, 290, 156/308.4, 517; 493/189, 193, 195, 199, 200, 931; 206/362, 438, 485, 574; 383/37, 39; 264/291, 292, 288.4

[56] References Cited

U.S. PATENT DOCUMENTS

| | | | |
|---|---|---|---|
| 3,181,751 | 5/1965 | Wilson | 383/39 |
| 3,254,828 | 6/1966 | Lerner | 383/37 |
| 3,749,237 | 7/1973 | Dorton | 206/438 |
| 3,844,865 | 10/1974 | Elton et al. | 156/229 |
| 3,884,412 | 5/1975 | Price | 229/69 |
| 4,234,086 | 11/1980 | Dorton | 383/37 X |

*Primary Examiner*—Donald E. Czaja
*Assistant Examiner*—Ramon R. Hoch
*Attorney, Agent, or Firm*—Powell L. Sprunger

[57] ABSTRACT

A sponge collecting device comprising, a backing sheet of flexible material having a front surface, a rear surface, a pair of side edges, and a pair of end edges connecting the side edges. The device has a plurality of pockets progressively disposed on the front surface of the backing sheet intermediate the end edges. The pockets comprise a first flap of flexible material having a pair of side edges, and an upper edge extending between the side edges. Side portions of the first flap adjacent its side edges are joined to the backing sheet adjacent the side edges of the backing sheet, and a lower portion of the first flap is joined to the backing sheet intermediate the joined side portions of the first flap. The upper edges of the first flap define an opening intermediate the first flap and backing sheet to receive sponges. The device has a plurality of second flaps of flexible material extending substantially the width of the first flaps between the side portions and having upper portions being joined to the backing sheet at a location above the upper edges of the first flaps. The second flaps extend downwardly past the upper edges of the associated first flaps to cover the openings of the pockets.

2 Claims, 3 Drawing Figures

50 17 48 52 44 42 16 14 46 40 30 16 14 46 50 48 17 18 32 34 38 32 34 38 10 12 20

METHOD FOR MAKING A SPONGE COLLECTING DEVICE

This is a continuation of application of Ser. No. 407,391, filed Aug. 12, 1982 now abandoned, which is a divisional of Ser. No. 223,187, filed Jan. 7, 1981, now abandoned.

BACKGROUND OF THE INVENTION

The present invention relates to collecting devices for surgical sponges.

During surgical procedures, absorbent sponges are utilized to absorb body fluids around the site of the surgical incision. The sponges are normally provided in two sizes, a 4-inch by 4-inch smaller sponge, and a 14-inch by 14-inch larger laparotomy sponge. In the past, when the wetted sponges were removed from the patient's body, they have been placed in a kick bucket for retention during the surgical procedure. At the end of the surgical procedure, the sponges were removed from the kick bucket, and were sorted according to size, after which they were counted to assure that no sponges were left in the patient's body. According to convention, the 4-inch by 4-inch sponges were counted in groups of ten, and the 14-inch by 14-inch sponges were counted in groups of five.

It will be apparent that the prior sorting and counting procedure was tedious and time consuming, and could be subject to error during the counting of sponges. A bag strip has been proposed with pockets in U.S. Pat. No. 3,749,237 in an attempt to facilitate this procedure. However, the openings of the pockets in this bag strip are left open, thus permitting possible contamination from the collected sponges through the air to the surgical site.

SUMMARY OF THE INVENTION

A principal feature of the present invention is the provision of an improved sponge collecting device of simplified construction.

The sponge collecting device comprises, a backing sheet of flexible material having a front surface, a rear surface, a pair of side edges, and a pair of end edges connecting the side edges. The device has a plurality of pockets progressively disposed on the front surface of the backing sheet intermediate the end edges. The pockets comprise a first flap of flexible material having a pair of side edges, and an upper edge extending between the side edges. Side portions of the first flap adjacent its side edges are joined to the backing sheet adjacent the side edges of the backing sheet, and a lower portion of the first flap is joined to the backing sheet intermediate the joined side portions of the first flap. The upper edge of the first flap defines an opening intermediate the first flap and backing sheet to receive sponges. The device has a plurality of second flaps of flexible material extending substantially the width of the first flaps between the side portions and having upper portions being joined to the backing sheet at a location above the upper edges of the first flaps.

A feature of the present invention is that soiled sponges may be placed in the pockets of the sponge collecting device.

Another feature of the invention is that the sponge collecting device facilitates counting of the soiled sponges.

Yet another feature of the invention is that the second flaps extend downwardly past the upper edges of the associated first flaps to cover the openings of the pockets.

Thus, a feature of the invention is that the second flaps may be utilized to cover the openings of the pockets after placement of soiled sponges in the pockets.

Yet another feature of the invention is that the second flaps minimize the possibility of contamination from the sponges through the air to the surgical site.

Further features will become more fully apparent in the following description of the embodiments of this invention and from the appended claims.

DESCRIPTION OF THE PREFERRED EMBODIMENTS

Figure 1:
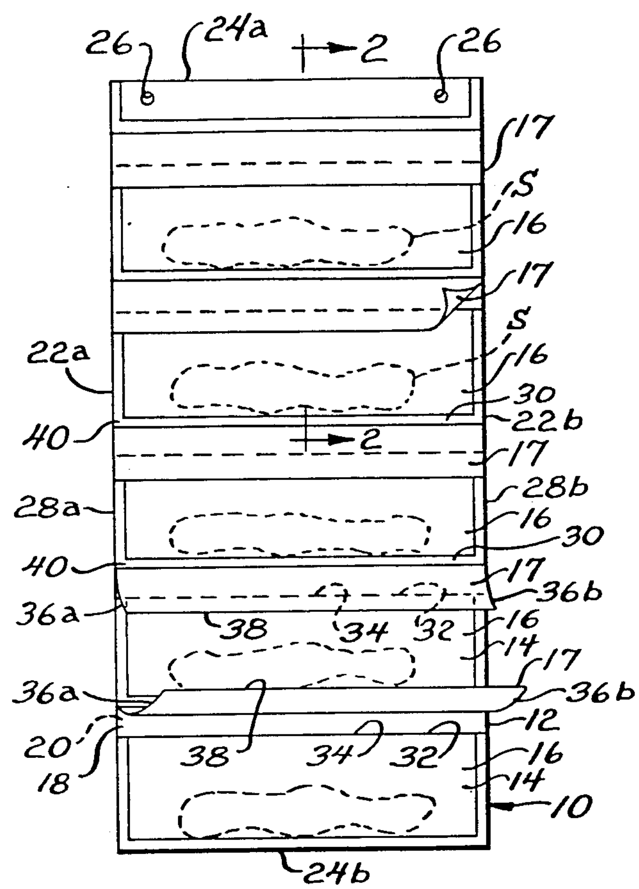
FIG. 1 is a front plan view of a sponge collecting device of the present invention.
Figure 2:
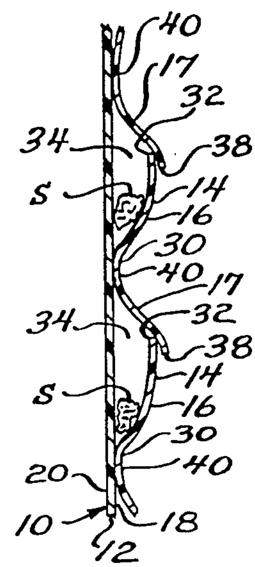
FIG. 2 is a fragmentary sectional view taken substantially as indicated along the line 2—2 of FIG. 1.

Referring now to FIGS. 1 and 2, there is shown a sponge collecting device generally designated 10 comprising a backing sheet 12 of flexible material, a plurality of pockets 14 each comprising a first flap 16 of flexible material joined to the backing sheet 12, and a plurality of second flaps 17. The backing sheet 12 and flaps 16 and 17 may be constructed from any suitable plastic material, such as polyethylene. The backing sheet 12 has a generally rectangular shape, and has a front surface 18, a rear surface 20, a pair of opposed side edges *22a* and *22b*, and a pair of opposed end edges *24a* and *24b* connecting the side edges *22a and b*. The backing sheet 12 may have a pair of spaced openings 26 located adjacent the end edge *24a* for suspending the device 10 from a suitable instrument received through the openings 26.

The first flaps 16 have a pair of opposed side edges *28a* and *28b*, a lower portion 30 extending between the side edges *28a* and *b*, and an upper edge 32 extending between the side edges *28a* and *b*. As shown, the side edges *28a* and *b* of the first flaps 16 are joined to the front surface 18 of the backing sheet 12 adjacent the side edges *22a* and *b* of the backing sheet 12 by suitable means, such as by heat sealing. Also, the lower portions 30 of the first flaps 16 are joined to the front surface 18 of the backing sheet 12 intermediate the flap side edges *28a* and *b*, by suitable means, such as by heat sealing. In this configuration, the upper edges 32 of the first flaps 16 define associated openings 34 intermediate the first flaps 16 and backing sheet 12 to receive soiled sponges in the pockets 14. Also, in this configuration, the pockets 14 are progressively disposed along the backing sheet 12 between the end edges *24a* and *b*. In a preferred form, the device 10 has five pockets 14 disposed along the backing sheet 12.

The second flaps 17 have a pair of opposed side edges *36a* and *36b* located adjacent the side edges *28a* and *b* of the first flaps 16, such that the second flaps 17 have a width approximately the width of the first flaps 16. The second flaps 17 have lower edges 38 extending between the side edges *36a* and *b*, and upper portions 40 joined to the front surface 18 of the backing sheet 12 by suitable means, such as by heat sealing. In a preferred form, the first flaps 16 are of one-piece construction with the second flaps 17 between the upper edges 32 of the first flaps 16 and the lower edges 38 of the second flaps 17, such that the lower portions 30 of the first flaps 16 are joined to the backing sheet 12 at the same location that the upper portions 40 of the second flaps 17 are joined to the backing sheet 12. As shown, the second flaps 17 have a sufficient length to extend downwardly past the upper edges 32 of the first flaps 16 such that the second flaps 17 cover the openings 34 of the first flaps 16 located below the second flaps 17.

Thus, in accordance with the present invention, five soiled sponges S may be placed in the five pockets 14 of the device 10, such that the device 10 facilitates collection and counting of the soiled sponges S. The second flaps 17 may be placed in overlapping relationship with the first flaps 16 in order to cover the openings 34 of the pockets 14. In this manner, the second flaps 17 close the pockets 14, and minimize the possibility of contamination from the sponges through the air to the surgical site.

Figure 3:
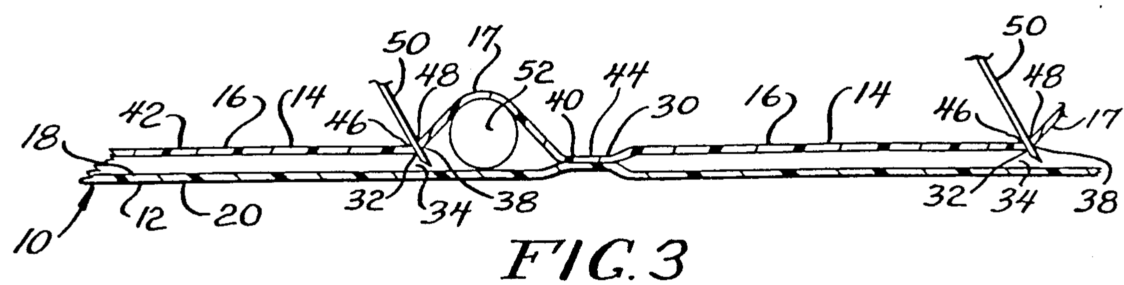
FIG. 3 is a sectional view illustrating a method of constructing the sponge collecting device of FIG. 1.

A method of constructing a sponge collecting device of the present invention is illustrated in connection with FIG. 3. A backing sheet 12 of flexible material is provided having a front surface 18, a rear surface 20, a pair of side edges, and a pair of end edges. A front sheet 42 of flexible material is placed over the front surface 18 of the backing sheet 12. The front sheet 42 is bonded to the backing sheet 12 along spaced lateral lines 44 which extend substantially between the side edges of the backing sheet 12. The front sheet 42 is severed along spaced upper and lower lateral lines 46 and 48, respectively, by suitable instruments, such as by knives 50. The upper and lower lateral lines 46 and 48 are located on opposed sides of the lateral bonding lines 44. Rods 52 are located beneath the front sheet 42 at a location intermediate the bonding lines 44 and the lower severance lines 48 in order to raise this portion of the front sheet 42. In this manner, the length of the front sheet 42 intermediate the bonding lines 44 and the lower severance lines 48 is increased while the front sheet 42 is severed along the lines 46 and 48. In this manner, the second flaps 17 located intermediate the bonding lines 44 and the lower severance lines 48 are formed having a sufficient length to overlap the upper portions of the first flaps 16 located intermediate the bonding lines 44 and the upper severance lines 46. Also, side portions of the front sheet 42 are bonded to the backing sheet 12 along spaced longitudinal lines extending from the lateral bonding lines 44 to the upper severance lines 46 at a location adjacent the side edges of the backing sheet 12. In this manner, the method of the present invention facilitates construction of the sponge collecting device 10 in order to form the first and second flaps 16 and 17 from the front sheet 42 on the backing sheet 12.

The foregoing detailed description is given for clearness of understanding only, and no unnecessary limitations should be understood therefrom, as modifications will be obvious to those skilled in the art.

I claim:

1. A method of constructing a sponge collecting device, comprising the steps of:

providing a backing sheet of flexible material having a front surface, a rear surface, a pair of side edges, and a pair of end edges;

placing a front sheet of flexible material over the front surface of the backing sheet;

bonding the front sheet to the backing sheet along a plurality of lateral lines extending substantially between the side edges of the backing sheet and spaced along the length of the sheets;

severing the front sheet along spaced upper and lower lateral lines on opposed sides of the lateral bonding lines while increasing the length of the front sheet at a location intermediate the bonding lines and the lower severance lines by moving the front sheet away from the backing sheet prior to severing by inserting an elongated member between the front sheet and backing sheet such that the portions of the front sheet intermediate the bonding lines and the lower severance lines have a sufficient length to overlap the portions of the front sheet intermediate the bonding lines and the upper severance lines; and bonding side portions of the front sheet to the backing sheet along longitudinal lines extending from the lateral bonding lines to the upper severance lines adjacent the side edges of the backing sheet.

2. A method if constructing a sponge collecting device, comprising the steps of:

providing a backing sheet of flexible material having a front surface and a rear surface;

placing a front sheet of flexible material over the front surface of the backing sheet;

bonding the front sheet to the backing sheet along a plurality of elongated lateral lines spaced along the length of the sheet;

severing the front sheet along spaced upper and lower lateral lines on opposed sides of the lateral bonding lines while increasing the length of the front sheet at a location intermediate the lateral bonding lines and the lower severance lines by moving the front sheet away from the backing sheet prior to severing by inserting an elongated member between the front sheet and backing sheet such that the portions of the front sheet intermediate the lateral bonding lines and the lower severance lines have a sufficient length to overlap the portions of the front sheet intermediate the lateral bonding lines and the upper severance lines; and bonding portions of the from sheet to the backing sheet along spaced longitudinal lines at locations extending from the lateral bonding lines to the upper severance lines of the front sheet.

* * * * *